(12) United States Patent
Zhang et al.

(10) Patent No.: US 8,374,370 B2
(45) Date of Patent: Feb. 12, 2013

(54) REAL EAR MEASUREMENT ADAPTOR WITH INTERNAL SOUND CONDUIT

(75) Inventors: Tao Zhang, Eden Prairie, MN (US); Brian Fideler, Jordan, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 479 days.

(21) Appl. No.: 12/414,876

(22) Filed: Mar. 31, 2009

(65) Prior Publication Data

US 2009/0245560 A1 Oct. 1, 2009

Related U.S. Application Data

(60) Provisional application No. 61/041,022, filed on Mar. 31, 2008.

(51) Int. Cl.
*H04R 25/02* (2006.01)

(52) U.S. Cl. .......... 381/330; 381/60; 381/322; 381/324; 381/381; 381/382

(58) Field of Classification Search ............. 381/60, 381/313, 314, 322, 324, 328, 330, 381, 382
See application file for complete search history.

(56) References Cited

U.S. PATENT DOCUMENTS

| | | | |
|---|---|---|---|
| 3,491,214 A * | 1/1970 | Rosemond et al. | 381/330 |
| 4,564,955 A | 1/1986 | Birch et al. | |
| 4,809,708 A | 3/1989 | Geisler et al. | |
| 5,386,475 A | 1/1995 | Birck et al. | |
| 5,711,308 A | 1/1998 | Singer | |
| 5,792,073 A | 8/1998 | Keefe | |
| 5,897,494 A | 4/1999 | Flock et al. | |
| 5,987,146 A | 11/1999 | Pluvinage et al. | |
| 6,007,494 A | 12/1999 | Zenner et al. | |
| D431,294 S | 9/2000 | Barnard et al. | |
| 6,154,546 A | 11/2000 | Uvacek | |
| 6,674,862 B1 | 1/2004 | Magilen | |
| D506,258 S | 6/2005 | Nielsen | |
| 7,239,711 B1 | 7/2007 | Andersen et al. | |
| 7,599,508 B1 * | 10/2009 | Lynch et al. | 381/330 |
| 7,756,283 B2 | 7/2010 | Bramslow | |
| 7,778,424 B2 | 8/2010 | Lange | |
| 8,059,847 B2 | 11/2011 | Nordahn | |
| 2002/0085729 A1 * | 7/2002 | Marx | 381/330 |
| 2004/0028250 A1 | 2/2004 | Shim | |
| 2004/0044389 A1 * | 3/2004 | Crawford | 607/116 |
| 2004/0234094 A1 | 11/2004 | Saunders et al. | |

(Continued)

FOREIGN PATENT DOCUMENTS

| | | |
|---|---|---|
| AU | 5830898 A | 9/1998 |
| AU | 2010200103 B2 | 7/2011 |

(Continued)

OTHER PUBLICATIONS

"Australian Application Serial No. 2009201228, First Examiner Report mailed Apr. 23, 2010", 1 Pg.

(Continued)

*Primary Examiner* — Allan R Wilson

(74) *Attorney, Agent, or Firm* — Schwegman, Lundberg & Woessner, P.A.

(57) ABSTRACT

Methods and apparatus for a hearing assistance device housing for use in real ear measurements. The methods and apparatus for configuration of a hearing assistance device using an apparatus including an opening to receive a sound tube for real ear measurements and providing an opening for connection of a sound hook to a housing of the hearing assistance device.

21 Claims, 3 Drawing Sheets

U.S. PATENT DOCUMENTS

| | | | |
|---|---|---|---|
| 2005/0002539 A1 | 1/2005 | Nielsen | |
| 2006/0045282 A1 | 3/2006 | Reber | |
| 2006/0171550 A1* | 8/2006 | Bryant et al. | 381/330 |
| 2007/0009107 A1 | 1/2007 | Lange | |
| 2007/0217639 A1 | 9/2007 | Stirnemann | |
| 2008/0152178 A1* | 6/2008 | Topholm et al. | 381/330 |
| 2008/0194984 A1 | 8/2008 | Keefe | |
| 2008/0260192 A1 | 10/2008 | Yanz et al. | |
| 2008/0260193 A1* | 10/2008 | Westermann et al. | 381/330 |
| 2008/0298600 A1 | 12/2008 | Poe et al. | |
| 2009/0245525 A1 | 10/2009 | Zhang et al. | |
| 2009/0299215 A1 | 12/2009 | Zhang | |
| 2010/0202642 A1 | 8/2010 | LoPresti et al. | |
| 2010/0246869 A1 | 9/2010 | Zhang et al. | |
| 2010/0260343 A1 | 10/2010 | Recker et al. | |
| 2011/0098551 A1 | 4/2011 | Zhang | |

FOREIGN PATENT DOCUMENTS

| | | |
|---|---|---|
| AU | 2010201189 | 9/2011 |
| AU | 2009201227 B2 | 10/2011 |
| AU | 2009201228 B2 | 1/2012 |
| DE | 4327634 C1 | 6/1994 |
| EP | 0381608 A2 | 8/1990 |
| EP | 1448014 B1 | 10/2005 |
| EP | 1705950 A2 | 9/2006 |
| EP | 2107831 A2 | 10/2009 |
| WO | WO-8901315 A1 | 2/1989 |
| WO | WO-9931936 A1 | 6/1999 |
| WO | WO-0239784 A1 | 5/2002 |
| WO | WO 2005089016 A1 * | 9/2005 |
| WO | WO-2007045254 A1 | 4/2007 |
| WO | WO-2007045271 A1 | 4/2007 |
| WO | WO-2010016925 A1 | 2/2010 |

OTHER PUBLICATIONS

"European Application Serial No. 09250958.7, Extended European Search Report mailed Nov. 29, 2010", 5 pgs.

"Australian Application Serial No. 2009201228, Office Action Response Filed Aug. 3, 2011", 5 pgs.

"Australian Application Serial No. 2009201228, Subsequent Examiner Report mailed Jun. 23, 2011", 2 pgs.

"European Application Serial No. 09250958.7, Response filed Jun. 24, 2011 to Extended European Search Report mailed Nov. 29, 2010", 5 pgs.

"U.S. Appl. No. 12/102,602, Response filed Jul. 2, 2012 to Non Final Office Action mailed Apr. 4, 2012", 11 pgs.

"U.S. Appl. No. 12/414,889, Notice of Allowance mailed Jul. 18, 2012", 7 pgs.

"U.S. Appl. No. 12/414,889, Response filed Jun. 14, 2012 to Non Final Office Action mailed Dec. 15, 2011", 9 pgs.

"European Application Serial No. 08251441.5, Response filed Jul. 5, 2012 to Extended Search Report mailed Dec. 20, 2011", 15 pgs.

"European Application Serial No. 10250039.4, Extended Search Report mailed Apr. 16, 2012", 8 pgs.

"European Application Serial No. 10250568.2, Response filed Jul. 10, 2012 to Extended Search Report mailed Dec. 13, 2011", 11 pgs.

"U.S. Appl. No. 12/102,602, Non Final Office Action mailed Apr. 4, 2012", 7 pgs.

"U.S. Appl. No. 12/102,602, Response filed to Restriction Requirement mailed Dec. 8, 2011", 8 pgs.

"U.S. Appl. No. 12/102,602, Restriction Requirement mailed Nov. 8, 2011", 6 pgs.

"U.S. Appl. No. 12/130,764, Non-Final Office Action mailed Aug. 20, 2010", 8 pgs.

"U.S. Appl. No. 12/130,764, Preliminary Amendment mailed Jul. 21, 2008", 6 pgs.

"U.S. Appl. No. 12/130,764, Response filed Jul. 30, 2010 to Restriction Requirement mailed Jul. 29, 2010", 7 Pgs.

"U.S. Appl. No. 12/130,764, Restriction Requirement mailed Jul. 29, 2010", 9 pgs.

"U.S. Appl. No. 12/414,889, Non Final Office Action mailed Dec. 15, 2011", 11 pgs.

"U.S. Appl. No. 12/537,908 , Response filed Jan. 11, 2012 to Non Final Office Action mailed Oct. 11, 2011", 9 pgs.

"U.S. Appl. No. 12/537,908, Final Office Action mailed Mar. 15, 2012", 11 pgs.

"U.S. Appl. No. 12/537,908, Non Final Office Action mailed Oct. 11, 2011", 10 pgs.

"U.S. Appl. No. 12/537,908, Preliminary Amendment mailed Jun. 22, 2010", 3 pgs.

"U.S. Appl. No. 12/685,295, Non Final Office Action mailed Mar. 12, 2012", 7 pgs.

"U.S. Appl. No. 12/730,380, Non Final Office Action mailed Mar. 30, 2012", 10 pgs.

"U.S. Appl. No. 12/980,745, Preliminary Amendment mailed Feb. 14, 2011", 5 pgs.

"Australian Application Serial No. 2009201227, First Examiner Report mailed Apr. 20, 2010", 2 Pgs.

"Australian Application Serial No. 2009201227, Response filed Apr. 18, 2011 to First Examiner Report mailed Apr. 20, 2010", 9 pgs.

"Australian Application Serial No. 2010200103, First Examiner Report mailed Feb. 2, 2011", 2 pgs.

"Australian Application Serial No. 2010200103, Response filed Jul. 8, 2011 to First Examiner Report mailed Feb. 2, 2011", 5 pgs.

"Australian Application Serial No. 2010201189, Examiner Report mailed Mar. 11, 2011", 1 pg.

"Australian Application Serial No. 2010201189, Response filed May 19, 2011 to Examiner Report mailed Mar. 11, 2011", 1 pg.

"Australian Application Serial No. 2009280002, Office Action Mailed Mar. 23, 2012", 2 Pgs.

"European Application Serial No. 08251441.5, Extended Search Report mailed Dec. 20, 2011", 18 pgs.

"European Application Serial No. 09250957.9, Extended European Search Report mailed Dec. 13, 2010", 5 pgs.

"European Application Serial No. 09250957.9, Response filed Jul. 5, 2011 to Extended European Search Report mailed Dec. 13, 2010", 16 pgs.

"European Application Serial No. 10250568.2, Extended Search Report mailed Dec. 13, 2011", 8 pgs.

"European Application Serial No. 10250568.2, Office Action mailed Jan. 16, 2012", 2 pgs.

"European Application Serial No. 08251441.5, Partial European Search Report mailed Jul. 14, 2011", 5 pgs.

"International Application Serial No. PCT/US2009/004528, International Preliminary Report on Patentability mailed Feb. 17, 2011", 6 pgs.

"International Application Serial No. PCT/US2009/004528, Search Report mailed Oct. 13, 2009", 7 pgs.

"International Application Serial No. PCT/US2009/004528, Written Opinion mailed Oct. 13, 2009", 7 pgs.

Chan, C K, et al., "Estimation of Eardrum Acoustic Pressure And of Ear Canal Length From Remote Points In The Canal Length From Remote Points In The Canal", Journal of the Acoustical Society of America, vol. 87, No. 3, XP009035813 ISSN: 0001-4966, (Mar. 1, 1990), 1237-1247.

Dillon,Ph.D., Harvey, "Hearing Aids", 4.4 Practical Issues in Real-Ear Testing, (Jan. 1, 2001), 101-104.

Hudde, H, et al., "Methods for Estimating the sound pressure at the eardrum", Journal of the Acoustical Society of America, vol. 106, No. 4, XP012001248 ISSN: 0001-4966, (Oct. 1, 2009), 1977-1992.

Moodie, K Shane, et al., "Procedure for Predicting Real-Ear Hearing Aid Performance in Young Children", Am. Journal of Audiology, Am. Speech-Language-Hearing Association, 3(1), (Mar. 1, 1994), 23-31.

Munro, Kevin J, et al., "Measuring the Real-Ear to Coupler Difference Transfer Function with and Insert Earphone and a Hearing Instrument: Are they the same?", Ear and Hearing, 26(1), (Feb. 1, 2005), 27-34.

Pascal, Jerome, et al., "Linear and nonlinear model of the human middle ear", J. Acoust. Soc. Am., vol. 104, No. 3, Pt. 1, (Sep. 1998), 1509-1516.

Yanz, Jerry, et al., "Real Ear Measurement System Using Thin Tube", U.S. Appl. No. 60/912,343, filed Apr. 17, 2007, 19 pgs.

* cited by examiner

REAL EAR MEASUREMENT ADAPTOR WITH INTERNAL SOUND CONDUIT

RELATED APPLICATIONS

The present application claims the benefit under 35 U.S.C. 119(e) of U.S. Provisional Patent Application Ser. No. 61/041,022, filed Mar. 31, 2008, which is incorporated herein by reference in its entirety.

FIELD OF TECHNOLOGY

This application relates generally hearing assistance devices and more particularly to apparatus for making real ear measurements with a hearing assistance device.

BACKGROUND

Hearing assistance devices are used to improve hearing for wearers. Such devices include, but are not limited to, hearing aids. Real ear measurements attempt to measure the actual sound produced by the hearing assistance device in an ear canal of a wearer of the device. Without real ear measurements, the fitting software of the hearing assistance device estimates the sound pressure level in the ear canal based on average ear geometry. This may be highly inaccurate.

What is needed in the art is an improved system for real ear measurement. The system for real ear measurement should be available for use with various hearing assistance devices, such as hearing aids.

SUMMARY

The present subject matter provides method and apparatus for real ear measurement using a hearing assistance device fitted with an apparatus to pass sound sampled from an ear canal of a wearer to a microphone of the hearing assistance device. One embodiment provides a method for configuration of a hearing assistance device, comprising placing a cover onto the hearing assistance device housing, the cover including a sound tube port adapted for an acoustic connection to a microphone of the hearing assistance device, and attaching an earhook to the hearing assistance device housing, the earhook and housing mating using an opening in the cover.

One embodiment provides an apparatus for attaching to a hearing assistance device housing, comprising a first opening adapted to cover a portion of the housing, a port to receive a sound tube, and an opening for connection between the housing and an earhook. A number of variations for each of the embodiments are provided herein.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1A:
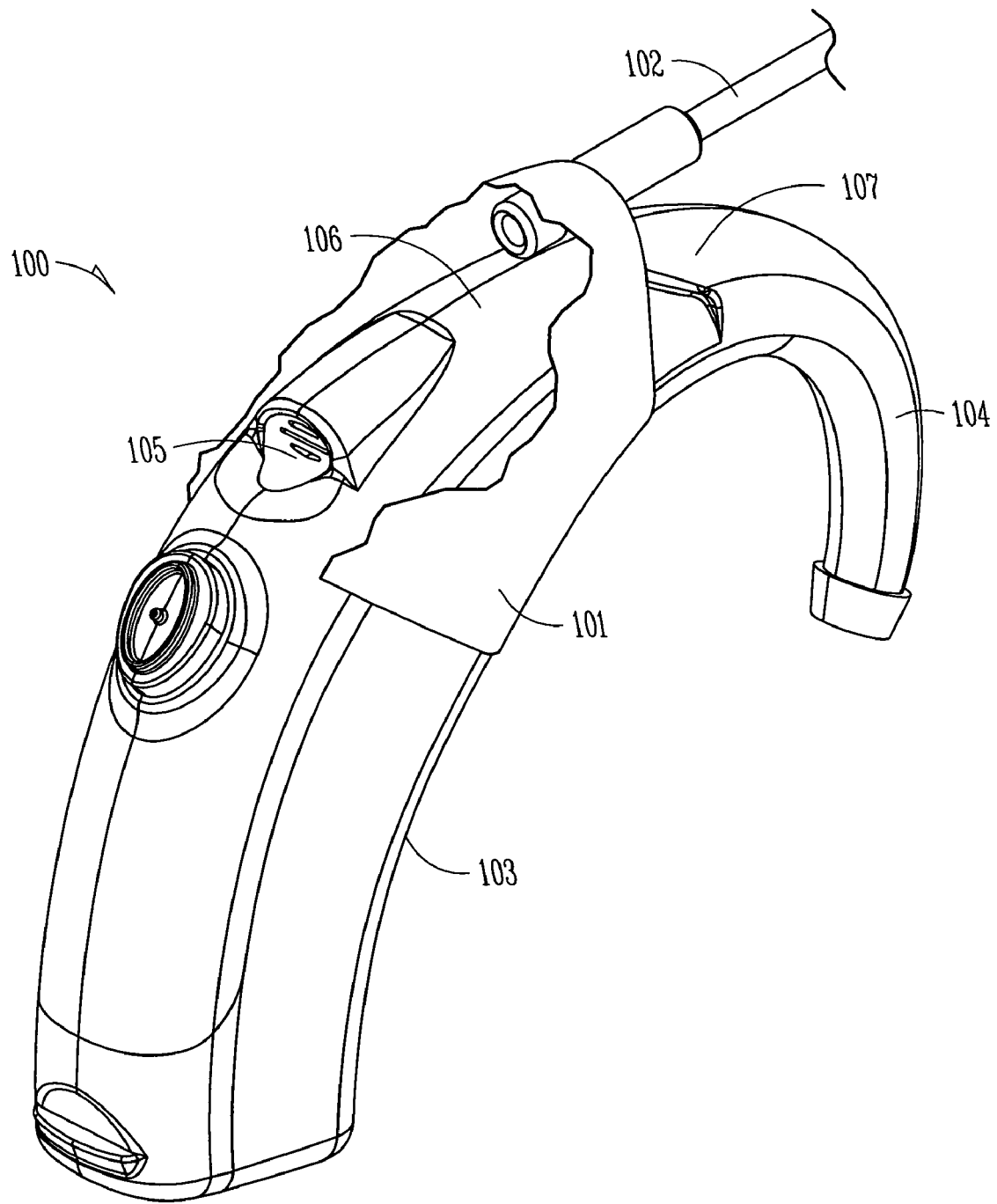
FIG. 1A shows a behind-the-ear hearing assistance device with a Real Ear Measurement (REM) adaptor according to one embodiment of the present subject matter.
Figure 1B:
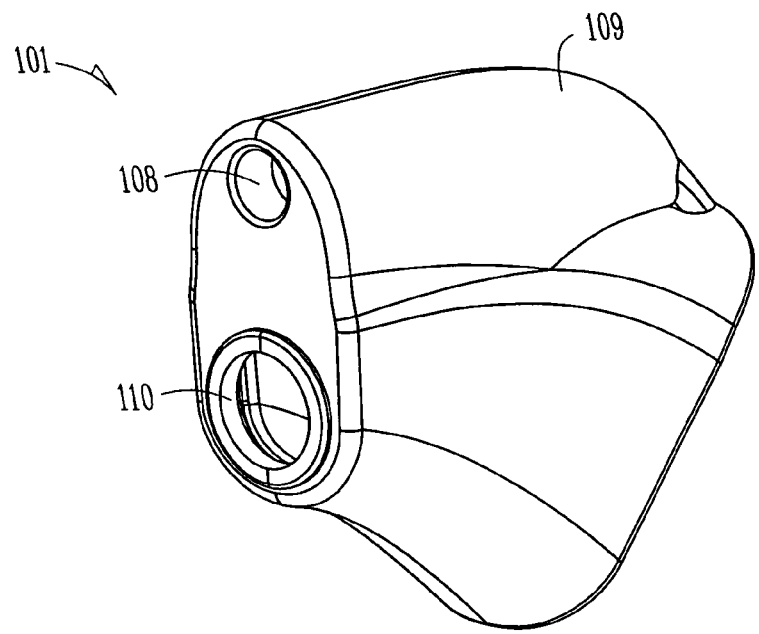
FIGS. 1B and 1C show different views of a REM adaptor according to one embodiment of the present subject matter.
Figure 1C:
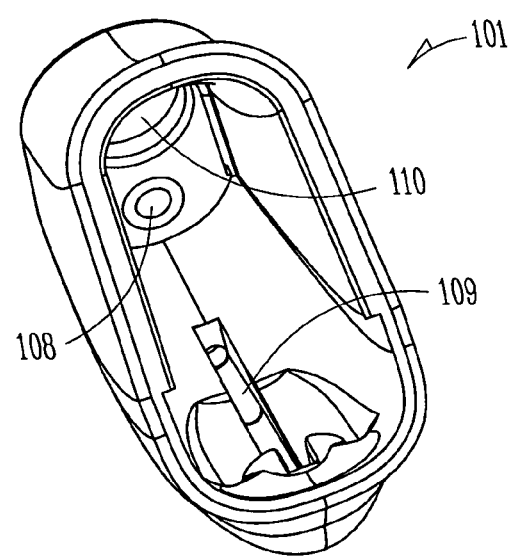

FIG. 1 shows a behind-the-ear hearing assistance device with a Real Ear Measurement (REM) adaptor according to one embodiment of the present subject matter. FIG. 1 shows a BTE type hearing assistance device 100, a cut-away view of a REM adaptor 101 and a partial view of an attached, thin sound tube, or REM tube 102. The sound tube for the BTE device is not shown, but connects to ear hook 104 and may terminate in any number of ear buds or ear molds (also not shown). FIGS. 1B and 1C show isolated views of the REM adaptor 101. The illustrated BTE type hearing assistance device 100 of FIG. 1 includes a main body 103, a ear hook 104 connected to a ear hook port, a rear microphone port 105 under a microphone hood 106 and a front microphone port 107 located near the earhook port. In general, the REM adaptor 101 is attached to a BTE hearing assistance device to assist in conducting real ear measurements of a user of the device using REM tube 102. Such real ear measurements use REM tube 102 to transfer sound from a user's ear canal to a microphone situated in the BTE housing. Real hear measurements provide more accurate results when ambient sound is isolated from the microphone, or microphones, used to make the measurement. More accurate results are also obtained when unused microphone(s) are acoustically sealed. The REM adaptor 101 provides a convenient way to convert the BTE hearing assistance device 100 to a real ear measurement device. Some materials and dimensions of REM tubes and connectors include, but are not limited to, those that are found in U.S. Provisional Patent Application Ser. No. 60/912,343, filed Apr. 17, 2007, entitled: REAL EAR MEASUREMENT SYSTEM USING THIN TUBE, the entire specification of which is hereby incorporated by reference. Thus, variations design and use may occur without departing from the scope of the present subject matter.

In the illustrated embodiment, the REM adaptor 101 is formed to fit tightly over a portion of the main body 103 of the BTE housing. The tight fit of the REM adaptor 101 provides isolation of acoustically sensitive components, such as microphones, enclosed in the BTE housing covered by the REM adaptor 101. The REM adaptor 101 includes a REM tube port 108 (FIG. 1B). The REM tube port 108 forms an airtight, acoustic seal around an inserted REM tube 102. Internally, (see FIGS. 1B and 1C) the REM adaptor 101 provides an acoustic conduit 109 from the REM tube port 108 to a desired microphone port of the BTE type hearing assistance device. Some BTE type hearing assistance devices include multiple microphones and microphone ports. In various embodiments, the REM adaptor 101 simultaneously seals unused microphone ports of the BTE type hearing assistance device while channeling sound from the REM tube 102 to a microphone used for real ear measurement. In the illustrated embodiment, the REM adaptor 101 seals the front microphone port using adaptor material located between the REM tube port 108 and an opening for the earhook port 110. The REM adaptor channels sound received using the REM tube 102 to the rear microphone port 105 using an acoustic conduit 109 formed in the adaptor 101. Additionally, the adaptor 101 insulates both microphones/microphone ports 105, 107 from undesirable ambient sound about the BTE type hearing assistance device 100. Variations of such designs include, but are not limited to an adaptor 101 that channels sound from the REM tube 102 to the front microphone port 107 while simultaneously isolating the rear microphone port 105 from ambient, as well as, REM tube sounds. Other embodiments of an REM adaptor provide acoustic conduits for channeling sound from the REM tube to multiple microphones and microphone ports enclosed in the BTE housing.

In various embodiments, the REM adaptor 101 is made from flexible and stretchable material for providing a tight fit when the REM adaptor 101 is applied to a BTE housing. For instance, rubber and elastomers are some examples of flexible, stretchable materials for making an REM adaptor 101.

The present subject matter presents a way to realize the REM functionality by employing a removable REM adaptor. REM can be measured when the REM adaptor is installed. Normal hearing aid functionality is supported when the REM adaptor is removed. One way to perform real ear measurement is to provide a way to get sound played in the ear canal back to a microphone on the device. This can be performed in a variety of ways, including, but not limited to, using a sound tube in the ear canal to route sound back to a microphone on the behind-the-ear or over-the-ear microphone. Since many hearing assistance devices include multiple microphones it is also beneficial to include a way to block sounds to any microphones that are not in use in order to isolate received sound to a single microphone and to eliminate unwanted room noise or other interferences during the real ear measurement. One way to perform this is to mechanically block any unwanted sounds by the use of an acoustical shield or cover.

In one embodiment of the present subject matter, real ear measurement (REM) is performed by first making a coupler response measurement and then following that with a real ear coupler difference measurement or RECD. Once an RECD is obtained, it can be used in a fitting to provide the audiologist accurate information as to the actual sound in the wearer's ear canal.

Coupler Response Measurement

Figure 2:
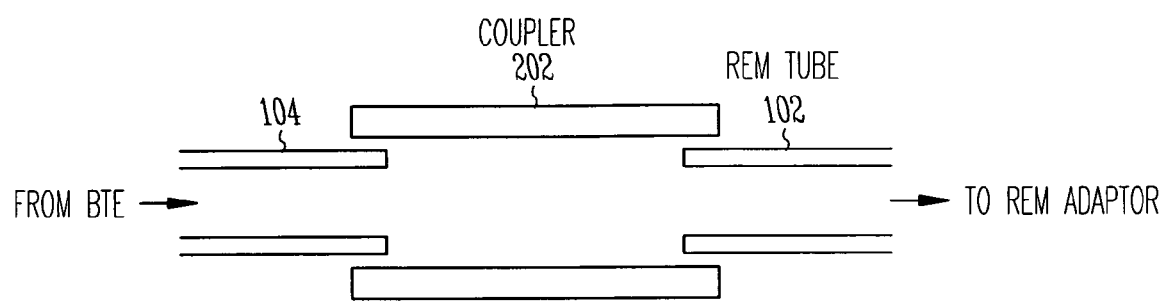
FIG. 2 shows an example of a coupler for measurements according to one embodiment of the present subject matter.

Before doing a REM, a coupler response measurement is performed at the factory or audiologist's office. In one embodiment, the coupler response is generated as follows: REM adaptor 101 is placed on the over or behind the ear unit and REM tube 102 is connected to REM tube port 108; a coupler response is calculated by connecting a coupler 202 to the BTE ear hook 104 and then the other side of the coupler is connected to the REM tube 102, as shown in FIG. 2; sound is played by the BTE 100 and sent to the earhook 104 using programming of the hearing assistance device and measured at the REM tube 102 and microphone of the hearing assistance device to which it is coupled; and the measured sound is subtracted from the sound that was played to get the coupler response.

Thus, Coupler Response=microphone response using sound tube in the coupler minus the sound played. In one embodiment, sound is played at 0-8 KHz at 100 Hz intervals, creating an 80 point matrix. However, this is just one example. Other intervals and ranges are possible without departing from the scope of the present subject matter.

Real Ear Coupler Difference Measurement

A real ear coupler difference measurement (RECD) is performed by: (1) placing the real ear measurement adaptor 101 over the hearing assistance device; (2) inserting the REM tube 102 into the port 108 of the REM adaptor 101; (3) placing the other end of the REM tube 102 inside any opening of an open ear mold/ear bud (or alongside a closed ear mold) so as to avoid bending the tube; (4) playing sound into the wearer's ear canal using a sound tube 200 connected to the earhook 104 of the BTE while recording sound received by the real ear microphone tube using the microphone on the behind-the-ear device; and (5) generating the real ear coupler difference (RECD) by the equation:

RECD=Real-ear response minus the Coupler Response.

Where the Real-ear response is given by:

Real-ear response=microphone response using sound tube in the real-ear minus the sound played.

In one embodiment, sound is played at 0-8 KHz at 100 Hz intervals, creating an 80 point matrix. However, this is just one example. Other intervals and ranges are possible without departing from the scope of the present subject matter.

Real Ear Measurement

When performing a real ear measurement, the REM adaptor 101 is installed to seal any unused microphone ports (e.g., seal the rear microphone port if the front microphone is being used to record real ear sounds and the directional device utilizes a static directional module). The real ear measurement microphone (e.g., front microphone) is coupled to the real ear measurement tube using an acoustic seal, and bending of the tube is minimized to avoid changing the response of the tube.

Normal Operation Mode

In normal operation all of the microphones are coupled to their respective sound ports. In some embodiments the hearing assistance device includes default ear hook information stored on the device and the coupler response information based on the standard ear hook. The coupler response for each device can be obtained in the production line. A flag is included to indicate that a calibration has been performed.

Initialization

When the hearing assistance device is first used with a default ear hook in the field, the following occurs according to one embodiment: the default ear hook information is used in the fitting software, the coupler response remains the same in some embodiments; and REM is performed such that the firmware uses the default REM stimulus. The stimulus is constructed to achieve similar signal-to-noise ratios across frequency The stimulus level is chosen to provide sufficient signal-to-noise ratio, but is still within the linear range of the receiver. The stimulus duration is chosen so that random interferences during the measurement can be reduced to a sufficient level via time-domain averaging. The default quality control values are used with the REM response to accept valid measurements and reject invalid measurements due to improper placement of the sound tube, improper coupling between the sound tube and the microphone or between ear hook and device, or a pinched or blocked sound tube. The RECD is calculated as the REM response minus the stored coupler response and the fitting is adjusted using the measured RECD.

Earhook and/or Receiver Tube Replacement

If a thin receiver tube of a particular length is used in the field for an open fitting, fitting is performed using the following steps, according to one embodiment:

the user selects the thin receiver tube of the correct length in the fitting software. In one approach the existing RECD values in the non-volatile memory, if any, are cleared. The firmware adjusts the REM stimulus to maintain a sufficient signal to noise ratio in the REM across frequencies. The stimulus level is adjusted to provide sufficient signal-to-noise ratio, but is still within the linear range of the receiver. The stimulus duration is chosen so that random interferences during the measurement can be reduced to a sufficient level via time-domain averaging. The new coupler response is derived using the default ear hook coupler response and the correction from the ear hook to the thin receiver tube in the fitting software. New quality control values can be used with the REM response to accept valid measurements and/or reject invalid measurements due to improper placement of the sound tube, improper coupling between the sound tube and the microphone or between ear hook and device, or a pinched or blocked sound tube. A new RECD is generated from the REM response minus the adjusted coupler response. Fitting is adjusted using the new RECD and the thin receiver tube information.

It is understood that different fitting systems and processes including different steps, order of steps, and apparatus can be derived from the present teachings that remain within the scope of the present subject matter. Processes for enhancing the real ear measurement data include, but are not limited to those fitting processes included in U.S. Provisional Patent Application Ser. No. 60/912,343, filed Apr. 17, 2007, entitled: REAL EAR MEASUREMENT SYSTEM USING THIN TUBE, the entire specification of which is hereby incorporated by reference.

This application is intended to cover adaptations and variations of the present subject matter. It is to be understood that the above description is intended to be illustrative, and not restrictive. The scope of the present subject matter should be determined with reference to the appended claim, along with the full scope of legal equivalents to which the claims are entitled.

What is claimed is:

1. A method for configuration of a hearing assistance device, comprising:
   placing a cover onto the hearing assistance device housing, the cover including a sound tube port adapted for an acoustic connection to a microphone port on the hearing assistance device housing; and
   attaching an earhook to the hearing assistance device housing, the earhook and housing mating using an opening for the earhook in the cover.

2. The method of claim 1, wherein placing includes acoustically sealing a second microphone port of the hearing assistance device.

3. The method of claim 1, further comprising coupling a first end of a sound tube with the sound tube port.

4. The method of claim 3, further comprising coupling a second end of the sound tube to a coupler.

5. The method of claim 4, further comprising coupling a second sound tube between the coupler and the earhook.

6. The method of claim 3, further comprising positioning a second end of the sound tube in an ear canal of a wearer.

7. The method of claim 6, wherein positioning includes inserting the second end of the sound tube through an opening of an ear bud.

8. The method of claim 6, further comprising:
   playing sound into the ear canal of the wearer;
   recording sound received by the sound tube using the microphone; and
   generating a real ear coupler difference (RECD) using the recorded sound.

9. The method of claim 1, further comprising playing a plurality of sounds having a frequency between 0 and 8000 hertz.

10. The method of claim 9, wherein the frequency of each sound of the plurality of sounds is separated in increments of about 100 hertz.

11. The method of claim 1, further comprising playing sound within a linear range of a receiver to provide a substantially equal signal-to-noise ratio across a range of sound frequencies.

12. An apparatus for attaching to a hearing assistance device housing, comprising:
   a first opening adapted to cover a portion of the housing;
   a port to receive a sound tube and adapted to pass sound to a first microphone port on the hearing assistance device housing when the apparatus is placed on the hearing assistance device housing; and
   an opening for an earhook, the opening adapted to provide for connection between the housing and the earhook.

13. The apparatus of claim 12, further comprising the sound tube coupled to the port.

14. The apparatus of claim 12, wherein at least a portion of the apparatus includes a flexible material.

15. The apparatus of claim 14, wherein the flexible material is rubber.

16. The apparatus of claim 14, wherein the flexible material is an elastomer material.

17. An apparatus for attaching to a hearing assistance device housing, comprising:
   a first opening adapted to cover a portion of the housing;
   a port to receive a sound tube and adapted to pass sound to a first microphone port of the hearing assistance device when the apparatus is placed on the hearing assistance device;
   an opening for connection between the housing and an earhook; and
   a portion adapted to acoustically seal a second microphone port.

18. The apparatus of claim 17, further comprising a sound tube coupled to the port.

19. The apparatus of claim 17, wherein at least a portion of the apparatus includes a flexible material.

20. The apparatus of claim 19, wherein the flexible material is an elastomer material or rubber.

21. A method for configuration of a hearing assistance device, comprising:
   placing a cover onto the hearing assistance device housing, the cover including a sound tube port adapted for an acoustic connection to a microphone of the hearing assistance device; and
   attaching an earhook to the hearing assistance device housing, the earhook and housing mating using an opening in the cover,
   wherein placing includes acoustically sealing a second microphone port of the hearing assistance device.

* * * * *

UNITED STATES PATENT AND TRADEMARK OFFICE
CERTIFICATE OF CORRECTION

| | |
|---|---|
| PATENT NO. | : 8,374,370 B2 |
| APPLICATION NO. | : 12/414876 |
| DATED | : February 12, 2013 |
| INVENTOR(S) | : Zhang et al. |

Page 1 of 1

It is certified that error appears in the above-identified patent and that said Letters Patent is hereby corrected as shown below:

On the Title Page, Item (56)

In column 2, under "Other Publications", line 1-2, delete ""Australian Application Serial No. 2009201228, First Examiner Report mailed Apr. 23, 20 10", 1 Pg.", therefor On page 2, in column 1, under "Other Publications", line 4, delete "Filed" and insert --filed--, therefor On page 2, in column 1, under "Other Publications", line 30, delete "mailed" and insert --filed--, therefor On page 2, in column 2, under "Other Publications", line 7, delete "mailed" and insert --filed--, therefor On page 2, in column 2, under "Other Publications", line 13, delete "mailed" and insert --filed--, therefor On page 2, in column 2, under "Other Publications", line 28, delete "Mailed" and insert --mailed--, therefor On page 2, in column 2, under "Other Publications", line 49, delete "C K," and insert --C. K.,--, therefor On page 2, in column 2, under "Other Publications", line 54, delete "Dillon,Ph.D" and insert --Dillon, Ph.D--, therefor On page 2, in column 2, under "Other Publications", line 56, delete "H," and insert --H.,--, therefor On page 2, in column 2, under "Other Publications", line 59, delete "K" and insert --K.--, therefor On page 2, in column 2, under "Other Publications", line 63, delete "J," and insert --J.,--, therefor Signed and Sealed this
Twenty-fifth Day of November, 2014

Michelle K. Lee
*Deputy Director of the United States Patent and Trademark Office*